(12) United States Patent
Kim et al.

(10) Patent No.: US 9,707,001 B2
(45) Date of Patent: Jul. 18, 2017

(54) PIN GUIDE FOR OPERATING ON AVASCULAR NECROSIS OF THE FEMORAL HEAD

(75) Inventors: Seok Jung Kim, Seoul (KR); Min Hyun Kim, Saddle River, NJ (US)

(73) Assignee: The Catholic University Industry—Academic Cooperation Foundation, Seoul (KR)

( * ) Notice: Subject to any disclaimer, the term of this patent is extended or adjusted under 35 U.S.C. 154(b) by 896 days.

(21) Appl. No.: 14/116,338

(22) PCT Filed: Dec. 29, 2011

(86) PCT No.: PCT/KR2011/010282
§ 371 (c)(1),
(2), (4) Date: Aug. 4, 2014

(87) PCT Pub. No.: WO2012/134038
PCT Pub. Date: Oct. 4, 2012

(65) Prior Publication Data
US 2015/0066041 A1    Mar. 5, 2015

(30) Foreign Application Priority Data
Mar. 31, 2011 (KR) ........................ 10-2011-0029379

(51) Int. Cl.
*A61B 17/17* (2006.01)
*A61B 17/92* (2006.01)

(52) U.S. Cl.
CPC .... *A61B 17/1721* (2013.01); *A61B 2017/922* (2013.01)

(58) Field of Classification Search
CPC .................................................. A61B 17/1721
See application file for complete search history.

(56) References Cited

U.S. PATENT DOCUMENTS

| | | | | |
|---|---|---|---|---|
| 2,301,500 A | * | 11/1942 | Anderson | A61B 17/1721 606/103 |
| 2,531,734 A | * | 11/1950 | Hopkins | A61B 17/1703 606/97 |
| 3,670,415 A | * | 6/1972 | Rose | A61B 17/2816 30/349 |
| 5,324,295 A | * | 6/1994 | Shapiro | A61B 17/1714 606/86 R |
| 8,123,699 B2 | * | 2/2012 | Lyon | A61B 17/3403 600/567 |

(Continued)

FOREIGN PATENT DOCUMENTS

| | | |
|---|---|---|
| JP | 4065908 B2 * | 6/2002 |
| JP | 2004-358057 A | 12/2004 |

(Continued)

*Primary Examiner* — David Bates
(74) *Attorney, Agent, or Firm* — Joseph Hyosuk Kim; JHK Law

(57) ABSTRACT

A pin guide for the surgical operation of an avascular necrosis of a femoral head includes a guide body having a central pin guide hole extending along a centerline of the guide body and a plurality of side pin guide holes formed so as to make a specified angle with the central pin guide hole. The side pin guide holes are radially arranged around the central pin guide hole at a front side of the guide body and joined to the central pin guide hole at a rear side of the guide body.

7 Claims, 4 Drawing Sheets

(56) References Cited

U.S. PATENT DOCUMENTS 9,023,051 B2 * 5/2015 Hanson .............. A61B 17/1764
378/205

FOREIGN PATENT DOCUMENTS

| KR | 10-2005-0123111 A | 12/2005 |
|----|-------------------|---------|
| KR | 10-2010-0030933 A | 3/2010  |
| WO | WO 2009-094239 A1 | 7/2009  |

* cited by examiner

PIN GUIDE FOR OPERATING ON AVASCULAR NECROSIS OF THE FEMORAL HEAD

TECHNICAL FIELD

The present invention relates to a pin guide for the surgical operation of an avascular necrosis of a femoral head capable of easily removing a wide area of necrosis lesion of a femur. The pin guide includes a guide body having a central pin guide hole and a plurality of side pin guide holes formed so as to make a specified angle with the central pin guide hole, the side pin guide holes radially arranged around the central pin guide hole at the front side of the guide body and joined to the central pin guide hole at the rear side of the guide body.

BACKGROUND ART

In general, an avascular necrosis of a femoral head refers to a disease in which a femoral head is dying off due to the block of blood flowing toward a femoral head. For many different causes, blood circulatory disturbance may occur in some or all regions of a femoral head. As a result, there appears to a progressive necrosis which destroys the femoral head and induces a secondary osteoarthritis.

Surgical treatment for an avascular necrosis of a femoral head are largely classified into a method of reviving an original joint and a method of replacing an original joint with an artificial joint. A femoral head drilling method or a core decompressing method is used as the method of reviving an original joint. In case of using these methods, a necrosis lesion of a femoral head is removed and then an operation for autogenous iliac bone graft and stem cell transplantation is carried out.

In this operation, a healthy spongy bone is removed from a hip joint bone of a patient. After getting rid of a dead bone of a femoral head, the spongy bone is transplanted by pressing the same against the femoral head. If it is not proper to use a patient's own iliac bone, a hip joint bone of other person is used. Use of a hip joint bone of other person poses a problem in that the post-operation physical adaptation period becomes longer. In case of transplanting a patient's own iliac bone, there is posed a problem in that the operation time grows longer and the pain felt by a patient after operation becomes acute.

As one example of instruments for the surgical operation of an avascular necrosis of a femoral head, there is known an instrument using a core decompression method, which includes: a center pin pressed against a necrosis lesion of a femoral head and formed into a needle-like rod structure having a specified diameter and a specified length; a core decompressor for performing a sawing operation by a predetermined distance from a femur surface to a necrosis lesion, the core decompressor having a middle portion guided by the center pin, the core decompressor attached to a drill hand piece at one end and provided with a cylindrical saw at the other end; a harvester inserted into a femur along a hole formed by the saw, the harvester configured to pick up a terminus portion of the sawed femur and to extract the terminus portion; and a pressing instrument for pressing the femur cell to enlarge the diameter thereof so that the femur cell extracted by the harvester can be re-entered into the hole and can be self-joined (see Korean Patent Application No. 10-2009-0128000 filed by the applicant of the subject application).

In the conventional instrument for the surgical operation of an avascular necrosis of a femoral head, a drill hole extending to a necrosis lesion is formed through the use of a drill. A center pin is inserted into the drill hole. Using the center pin as a guide, a decompressor is linearly moved forward. While repeatedly sawing a femur, the decompressor gains access to the necrosis lesion, thereby removing the necrosis lesion. However, the conventional instrument cannot remove a necrosis lesion larger in size than the outer diameter of the decompressor. For that reason, the conventional instrument suffers from a problem in that it is suitable for the removal operation of a narrow necrosis lesion but is not suitable for the removal operation of a wide necrosis lesion.

SUMMARY OF THE INVENTION

Technical Problem

In view of the aforementioned problems, it is an object of the present invention to provide a pin guide for the surgical operation of an avascular necrosis of a femoral head capable of easily removing a wide area of necrosis lesion of a femur.

Means for Solving the Problem

In order to achieve the above object, the present invention provides a pin guide for the surgical operation of an avascular necrosis of a femoral head, including: a guide body having a central pin guide hole extending along a centerline of the guide body and a plurality of side pin guide holes formed so as to make a specified angle with the central pin guide hole, the side pin guide holes radially arranged around the central pin guide hole at a front side of the guide body and joined to the central pin guide hole at a rear side of the guide body.

In the pin guide, the guide body may have a length of 8 to 10 cm, preferably 9 cm. It is preferred that the side pin guide holes are formed at upper, lower, left and right sides of the central pin guide hole at a regular interval of 90 degrees.

It is preferred that each of the side pin guide holes makes an angle of 4 to 10 degrees with the central pin guide hole.

The guide body may have a slot formed on one side thereof to extend along a longitudinal direction of the guide body. It is preferred that an anchor member is slidably fitted to the slot and can be configured to be fixed to a femur.

The anchor member is a contact portion with the femur. The anchor member may have two or more blind holes to which anchor needles are fitted, and the anchor needles protruding from the blind holes so as to be fixed to the femur.

The pin guide may further include: a handle attached to an outer surface of the guide body.

Effects of the Invention

According to the pin guide for the surgical operation of an avascular necrosis of a femoral head, the guide body has a central pin guide hole extending along a centerline of the guide body and a plurality of side pin guide holes formed so as to make a specified angle with the central pin guide hole. The side pin guide holes are radially arranged around the central pin guide hole at a front side of the guide body and are joined to the central pin guide hole at a rear side of the guide body. Therefore, the pin guide makes it possible to easily remove a wide area of necrosis lesion of a femur.

In addition, the femur pieces obtained in the surgical operation of an avascular necrosis of a femoral head are not wasted but transplanted to the patient femur. It is therefore possible to increase the physical adaptation of a patient after the surgical operation. This eliminates to use other person's femur pieces or femur pieces removed from other portions of a patient's own femur. Consequently, it becomes possible to significantly shorten the operation time.

BEST MODE FOR CARRYING OUT THE INVENTION

A preferred embodiment of the present invention will now be described with reference to the accompanying drawings.

Figure 1:
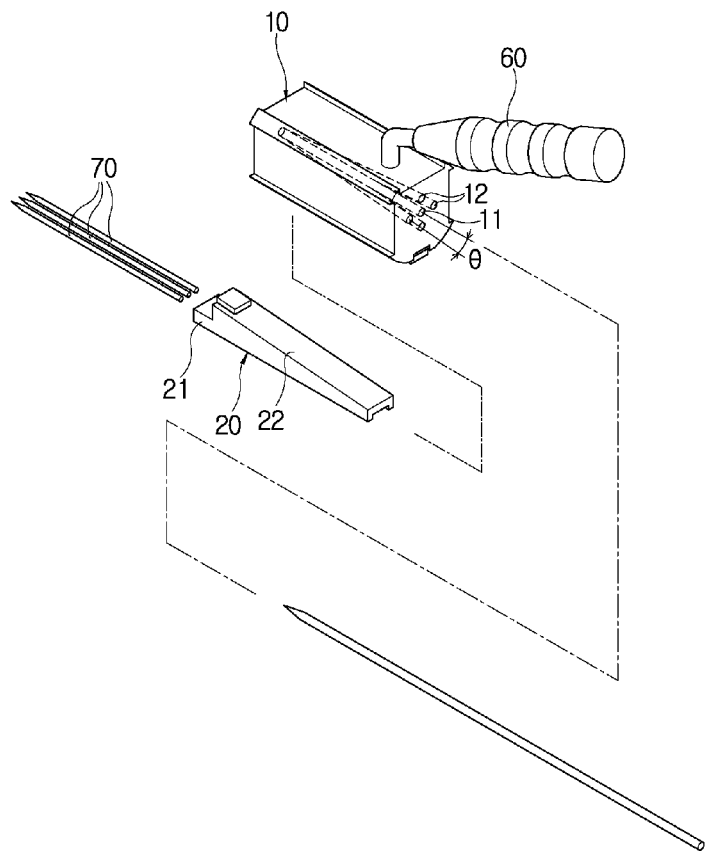
FIG. 1 is an exploded perspective view showing a pin guide for the surgical operation of an avascular necrosis of a femoral head according to the present invention.
Figure 2:
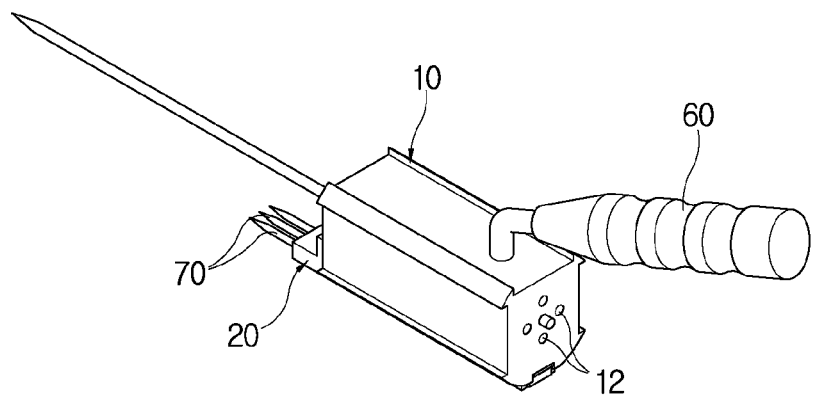
FIG. 2 is an assembled perspective view showing the pin guide for the surgical operation of an avascular necrosis of a femoral head according to the present invention.
Figure 3:
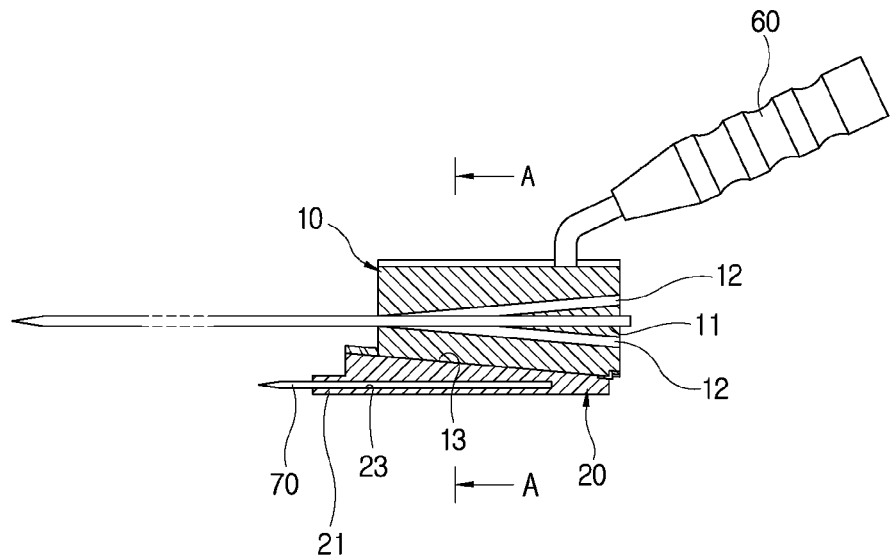
FIG. 3 is a section view showing the pin guide for the surgical operation of an avascular necrosis of a femoral head according to the present invention.
Figure 4:
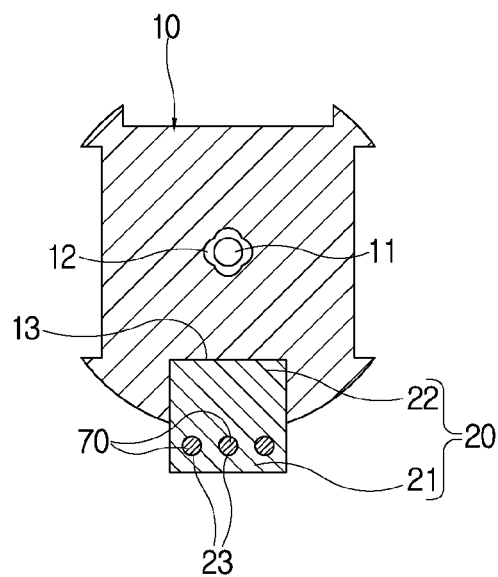
FIG. 4 is a section view of the pin guide taken along line A-A in FIG. 3.
Figure 5:
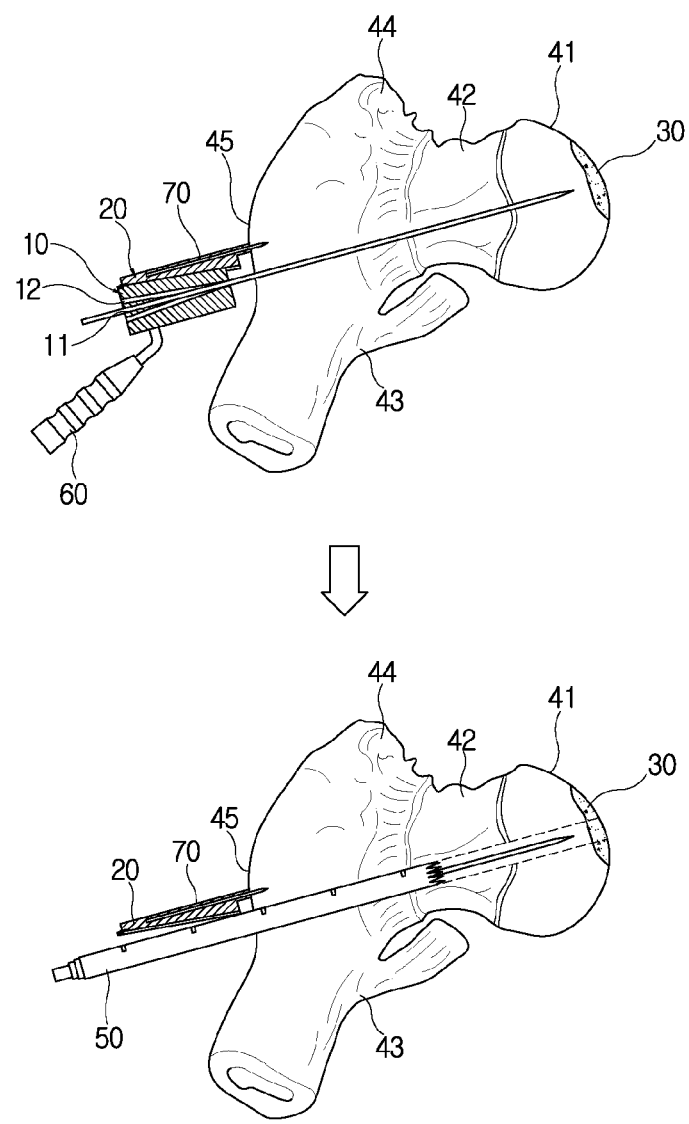
FIGS. 5 and 6 are front views illustrating a surgical operation process performed using the pin guide for the surgical operation of an avascular necrosis of a femoral head according to the present invention.
Figure 6:
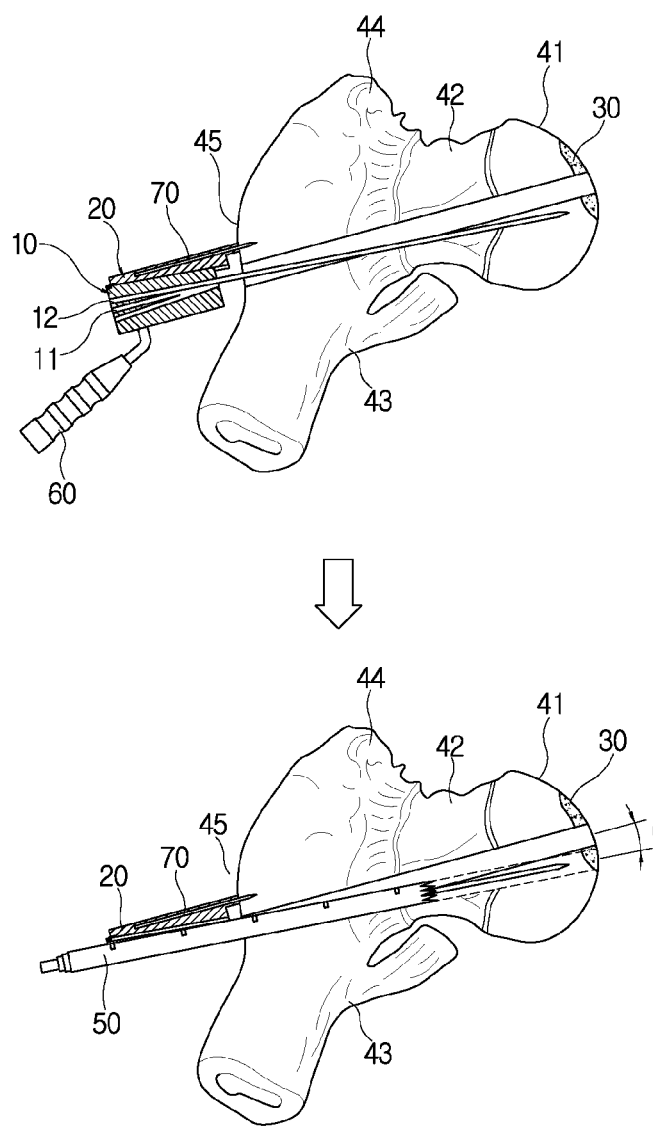

FIG. 1 is an exploded perspective view showing a pin guide for the surgical operation of an avascular necrosis of a femoral head according to the present invention. FIG. 2 is an assembled perspective view showing the pin guide for the surgical operation of an avascular necrosis of a femoral head according to the present invention. FIG. 3 is a section view showing the pin guide for the surgical operation of an avascular necrosis of a femoral head according to the present invention. FIG. 4 is a section view of the pin guide taken along line A-A in FIG. 3. FIGS. 5 and 6 are front views illustrating a surgical operation process performed using the pin guide for the surgical operation of an avascular necrosis of a femoral head according to the present invention.

Referring to FIGS. 1 to 4, the pin guide for the surgical operation of an avascular necrosis of a femoral head according to the present invention includes a guide body 10 having a central pin guide hole 11 formed in the guide body 10 and a plurality of side pin guide holes 12 formed in the guide body 10 so as to make a specified angle with the central pin guide hole 11.

More specifically, the guide body 10 is formed into different shapes, e.g., a rectangular shape, a cylindrical shape, a polygonal shape or a trapezoidal shape. The central pin guide hole 11 is formed at the center of the guide body 10 so that a center pin can be inserted into the central pin guide hole 11.

Preferably, a handle 60 gripped by a user during surgical operation or during transportation is arranged in one outer end portion of the guide body 10.

If the guide body 10 is too short or too long, it becomes inconvenient to perform the surgical operation. Therefore, it is preferred that the length of the guide body 10 is set substantially equal to 9 cm in order to facilitate the surgical operation.

The central pin guide hole 11 serves to guide the center pin so that the center pin can accurately gain access to an avascular necrosis lesion of a femoral head. The central pin guide hole 11 is formed along the centerline of the guide body 10 and have a diameter substantially equal to the diameter of the center pin. In general, the center pin has a diameter of 2 to 4 cm and, therefore, the diameter of the central pin guide hole 11 is set substantially equal to 2 to 4 cm.

The side pin guide holes 12 are formed in the guide body 10 so as to have a diameter substantially equal to the diameter of the pin. The side pin guide holes 12 are radially arranged around the central pin guide hole 11 at the front side of the guide body 10 as shown in FIG. 2 and are joined to the central pin guide hole 11 at the rear side of the guide body 10 as can be seen in FIG. 3.

More specifically, the inlets of the side pin guide holes 12 radially arranged around the central pin guide hole 11 at the front side of the guide body 10. The outlets of the side pin guide holes 12 are formed at the rear side of the guide body 10 so as to meet the outlet of the central pin guide hole 11. Therefore, the side pin guide holes 12 are spaced apart from the central pin guide hole 11 at the front side of the guide body 10 but are joined to the central pin guide hole 11 at the rear side of the guide body 10. Thus, the side pin guide holes 12 make a specified angle with the central pin guide hole 11.

In this regard, the angle θ of the side pin guide holes 12 with respect to the central pin guide hole 11 is set preferably equal to 4 to 10 degrees and more preferably equal to 5 degrees. This is because, if the length of the guide body 10 is 9 cm and if the angle θ between the side pin guide holes 12 and the central pin guide hole 11 is 5 degrees, it becomes possible to perform a surgical operation with respect to a necrosis lesion 30 of a femoral head regardless the size of the necrosis lesion 30.

The size of femurs differs from person to person. For that reason, if the size of the pin guide according to the present invention is set in conformity with the size of a largest femur, it is impossible to perform a surgical operation with respect to a femur having a smaller size. In the pin guide according to the present invention, the length of the guide body 10 is set into 9 cm and the angle θ between the side pin guide holes 12 and the central pin guide hole 11 is set into 5 degrees in conformity with the size of a smallest femur. Thus, it is possible to perform a surgical operation with respect to a necrosis lesion 30 of a femoral head regardless the size of the necrosis lesion 30.

It is preferred that, when seen from the front side of the guide body 10, the inlets of the side pin guide holes 12 are formed at the upper, lower, left and right sides of the central pin guide hole 11 at a regular interval of 90 degrees around the central pin guide hole 11. If the side pin guide holes 12 are arranged in all directions in this manner, it is possible to easily remove the necrosis lesion 30 regardless of the size thereof.

A slot 13 is formed on the side surface of the guide body 10. A anchor member 20 is slidably fitted to the slot 13. The slot 13 is formed to extend along the longitudinal direction of the guide body 10 and is opened outward.

The anchor member 20 includes an upper end portion 21 which is exposed from the slot 13 when the anchor member 20 is fitted to the slot 13 and a lower end portion 22 which is positioned lower than the upper end portion 21 and is fitted to the slot 13. Two or more blind holes 23 are formed in the upper end portion 21 of the anchor member 20. Anchor needles 70 are fitted to the blind holes and are used to fix the anchor member 20 to the outer surface 45 of a femur. The lower end portion 22 of the anchor member 20 is formed into a shape conforming to the shape of the slot 13 so that the lower end portion 20 can be fitted to the slot 13.

The slot 13 of the guide body 10 and the anchor member 20 can be coupled by means of a dovetail joint so that the anchor member 20 can be slidably fitted to, and strongly secured to the slot 13. The upper end portion 21 of the anchor member 20 can be fixed to the outer surface 45 of a femur.

When performing a surgical operation for the removal of a necrosis lesion 30, the upper end portion 21 of the anchor member 20 is fixed to the outer surface 45 of a femur. In this state, the pin can be stably driven into the femur through the central pin guide hole 11 or one of the side pin guide holes 12. After the pin is driven into the femur, the guide body 10 is detached from the anchor member 20 by pulling the guide body 10 backward so that the guide body 10 can be slide along the anchor member 20.

As described above, the pin guide for the surgical operation of an avascular necrosis of a femoral head according to the present invention can remove a wide necrosis lesion 30 because the side pin guide holes 12 are formed in the guide body 10 so that the pin can be driven into the femur at an increased angle with respect to the central pin guide hole 11. Description will now be made on a surgical operation performed using the pin guide of the present invention.

First, a surgical operation for the removal of a necrosis lesion 30 using the central pin guide hole 11 will be described. A femoral neck 42 is positioned below the femoral head 41. A major trochanter 44 and a minor trochanter 43 are arranged below the femoral neck 42. In case where a necrosis lesion 30 is generated at the tip end of the femoral head 41, an operator performs a surgical operation at an operation position opposite to the necrosis lesion 30.

The operation position is set so as not to cause any damage on the outer surface of the femoral neck 42. Therefore, it is preferred that the operation position is set in alignment with the center of the necrosis lesion 30 and the femoral neck 42. If the operation position is set in this manner, the upper end portion 21 of the anchor member 20 is fixed to the femur with the rear surface of the guide body 10 pressed against the outer surface 45 of the femur as shown in an upper diagram of FIG. 5.

In a state in which the guide body 10 is fixed to the femur, the center pin is inserted into the central pin guide hole 11 so as to face the necrosis lesion 30. In general, the distance from the outer surface 45 of the femur to the femoral head 41 is approximately 9 to 10 cm and the length of the center pin is about 12 to 15 cm. When driven into the femur, the center pin protrudes about 5 to 7 cm from the outer surface 45 of the femur.

After the center pin is driven into the femur, the guide body 10 is pulled backward and is separated from the anchor member 20. Then, as shown in a lower diagram of FIG. 5, the femur is drilled with a decompressor 50 which moves along the center pin. The decompressor 50 is driven by a drill hand piece. The decompressor 50 continues to drill the femur until the necrosis lesion 30 is removed. By drilling the femur with the decompressor 50, a tunnel 46 extending through the necrosis lesion 30 is formed as shown in an upper diagram of FIG. 6. In the surgical operation using the central pin guide hole 11, only a central portion of the necrosis lesion 30 is partially removed. In order to remove the remaining portion of the necrosis lesion 30, it is necessary to use the side pin guide holes 12 which makes a specified angle with the central pin guide hole 11.

Next, description will be made on a surgical operation for the removal of the remaining portion of the necrosis lesion 30 using the side pin guide holes 12. After partially removing the central portion of the necrosis lesion 30 along the center pin, the center pin is pulled out from the femur. The guide body 10 is coupled again to the anchor member 20 which stays fixed to the outer surface 45 of the femur. In this state, the pin is inserted into one of the side pin guide holes 12 and the femur is drilled using the decompressor 50. For example, the pin is inserted into the respective side pin guide holes 12 one after another in the order of the upper, lower, left and right side pin guide holes 12, during which time the femur is drilled by the decompressor 50.

More specifically, as shown in an upper diagram of FIG. 6, the pin is inserted into the upper side pin guide hole 12 among the radially-arranged side pin guide holes 12 and is driven into the femur from the outer surface 45 of the femur toward the necrosis lesion 30. Since the upper side pin guide hole 12 makes an angle of 5 degrees with the central pin guide hole 11, the tip end of the pin driven into the femur moves toward the lower portion of the necrosis lesion 30 through the upper side pin guide hole 12 while making an angle of 5 degrees with the central pin guide hole 11.

If the pin is completely driven into the femur through the upper side pin guide hole 12, the guide body 10 is detached from the anchor member 20 and the decompressor 50 is moved forward along the pin to drill the femur and remove the lower portion of the necrosis lesion 30.

Similarly, the upper, left and right portions of the necrosis lesion 30 are removed through the use of the lower, left and right side pin guide holes 12. Consequently, a hopper-shaped tunnel 46 having a width growing larger from the outer surface 45 of the femur toward the necrosis lesion 30 is formed in the femur. Therefore, even if the necrosis lesion 30 is generated over a wide area of the femoral head 41, it is possible to easily remove the necrosis lesion 30 through the use of the side pin guide holes 12 making a specified angle with the central pin guide hole 11. Needless to say, the patient's own femur pieces generated during the removal of the necrosis lesion 30 are transplanted to the tunnel 46 formed in the femur during the process of the surgical operation.

As set forth above, the pin guide for the surgical operation of an avascular necrosis of a femoral head according to the present invention includes the guide body 10 having the central pin guide hole 11 and the side pin guide holes 12 formed so as to make a specified angle with the central pin guide hole 11, the side pin guide holes 12 radially arranged around the central pin guide hole 11 at the front side of the guide body 10 and joined to the central pin guide hole 11 at the rear side of the guide body 10. Thus, the necrosis lesion 30 formed over a wide area of the femoral head 41 can be completely removed by cutting the necrosis lesion 30 and taking out residual femur pieces with a tool such as a curette or the like.

If the area of the necrosis lesion 30 is wide, the necrosis lesion 30 is removed using both the central pin guide hole 11 and the side pin guide holes 12. In contrast, if the area of the necrosis lesion 30 is narrow, the surgical operation for the removal of the necrosis lesion 30 can be performed using only the central pin guide hole 11.

While one preferred embodiment of the present invention has been described above, the present invention is not limited thereto but may be modified in many different forms without departing from the spirit and scope of the present invention.

What is claimed is:

1. A pin guide for surgical operation of avascular necrosis of a femoral head of a femur, comprising:
   a guide body having a central pin guide hole extending along a centerline extending in a longitudinal direction of the guide body and a plurality of side pin guide holes formed so as to make a specified angle with the central pin guide hole, the side pin guide holes radially arranged around the central pin guide hole at a rear side of the guide body and joined to the central pin guide hole at a front side of the guide body;
   wherein the guide body has a slot formed on one side thereof to extending in the longitudinal direction of the guide body,
   wherein the guide body further comprises an anchor member slidably fitted to the slot and configured to be fixed to the femur, the slot and the anchor member being coupled by means of a dovetail joint,
   wherein the guide body is configured to be detached from the anchor member by pulling the guide body in the rear direction relative to the anchor member.

2. The pin guide of claim 1, wherein the guide body has a length of 8 to 10 cm.

3. The pin guide of claim 1, wherein the side pin guide holes are formed at upper, lower, left and right sides of the central pin guide hole at a regular interval of 90 degrees.

4. The pin guide of claim 1, wherein each of the side pin guide holes makes an angle of 4 to 10 degrees with the central pin guide hole.

5. The pin guide of claim 1, wherein the anchor member comprises a lower end portion fitted to the slot and an upper end portion protruding from the slot, and the lower end portion and the upper end portion are integrally formed.

6. The pin guide of claim 5, wherein the upper end portion has two or more blind holes to which anchor needles are fitted, the anchor needles protruding from the blind holes so as to be fixed to the femur.

7. The pin guide of claim 1, further comprising: a handle attached to an outer surface of the guide body.

* * * * *